United States Patent [19]

Patchornik et al.

[11] 4,215,219
[45] Jul. 29, 1980

[54] REAGENTS FROM PHENOLIC AND 8-HYDROXYQUINOLINIC ALDEHYDE OXIMES

[75] Inventors: Avraham Patchornik, Ness-Ziona; Abraham Warshawsky, Rehovot; Matityahu Fridkin, Cholon; Rami Kalir, Rehovot, all of Israel

[73] Assignee: Yeda Research and Development Co. Ltd., Rehovot, Israel

[21] Appl. No.: 802,897

[22] Filed: Jun. 2, 1977

Related U.S. Application Data

[62] Division of Ser. No. 545,220, Jan. 29, 1975, Pat. No. 4,085,261.

[30] Foreign Application Priority Data

Feb. 8, 1974 [IL] Israel ........................................ 44168

[51] Int. Cl.² .................. C07D 215/14; C07C 119/00
[52] U.S. Cl. ............................ 546/179; 260/566 A
[58] Field of Search .................. 260/566 A; 546/179

[56] References Cited

PUBLICATIONS

Morrison & Boyd, "Organic Chemistry," pp. 376–382 (1973).
Degering, "An Outline of Organic Nitrogen Compounds," p. 176 (1950).
Flett, Chemistry and Industry, Aug. 6, 1977, pp. 641–646.

*Primary Examiner*—Norman Morgenstern
*Assistant Examiner*—L. Hendriksen
*Attorney, Agent, or Firm*—Browdy and Neimark

[57] ABSTRACT

A process for producing reagents useful in organic synthesis, for removing metal values from solutions thereof, for the capture of aldehydes, of the general formula

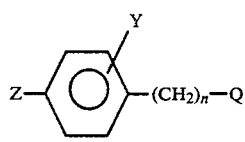

wherein Z designates a recurring part (CH$_2$—CH—CH$_2$) of a polymeric backbone of a polymer like polystyrene, of a copolymer comprising polystyrene and divinylbenzene, and butadiene, or other copolymers comprising styrene moieties; or wherein Z is the aliphatic moiety of a long-chain aralkyl compound having a terminal aryl group; or wherein Z designates alkyl; corresponding compounds wherein instead of the optionally substituted phenyl group there is present an optionally substituted naphthyl group; wherein n is an integer of from 1 to 15, and wherein Q designates a group selected from:

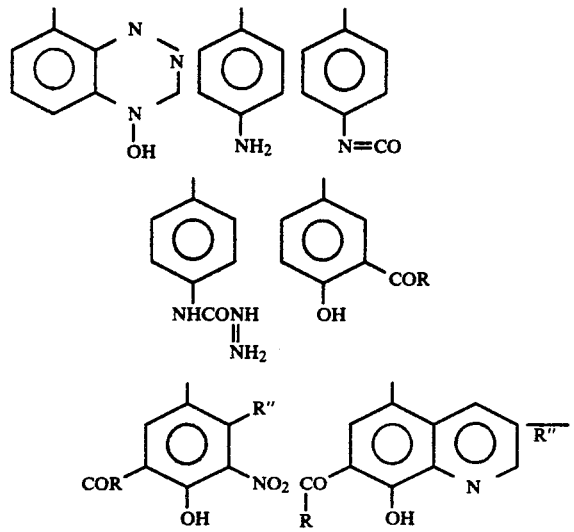

wherein R designates —H, lower alkyl, aryl, which may be substituted and wherein R" designates —H, alkyl, aryl, halogen, nitro or carboxy, or

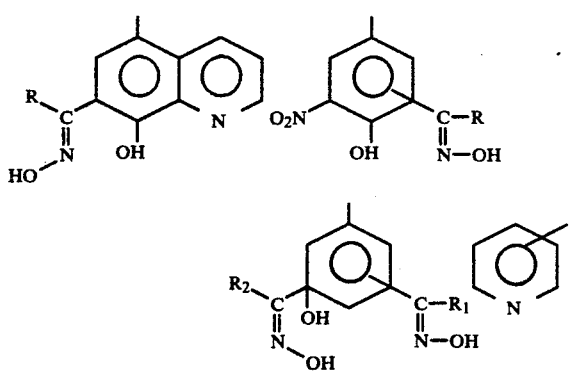

wherein R is —H, lower alkyl, aryl (which may be substituted), R$_1$ is —H, alkyl, aryl (which may be substituted), R$_2$ is —H, alkyl, aryl or substituted aryl, and wherein Y is —H or a non-interferring substituent, which comprises chemically binding an activated chemical moiety to a group

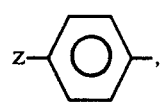

or a corresponding naphthyl-containing group, wherein Z is as defined above, according to the reaction scheme:

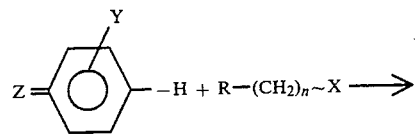  →  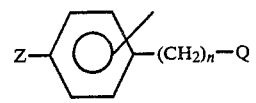
wherein Q is as defined above, or a functional group which can be converted to such group after the chemical bonding; and X is —Cl or —Br.
4 Claims, No Drawings

REAGENTS FROM PHENOLIC AND 8-HYDROXYQUINOLINIC ALDEHYDE OXIMES

This is a division, of application Ser. No. 545,220, filed Jan. 29, 1975 now U.S. Pat. No. 4,085,261.

The present invention relates to novel ion exchange agents and to a process for preparing these. Various polymeric substances were prepared hitherto, which contain certain desired functional moieties, adapted to carry out a specific activity. According to the methods used hitherto, such polymeric agents are prepared by a sequence of steps, and generally there take place certain undesired side-reactions, which result in cross-linking side-reactions and in undesired physical properties of the products. It is stressed that the novel process of the present invention results in substantially improved products, which have advantageous physical and chemical properties. The advantageous properties of the products obtained according to the present invention are a direct result from the method of preparation of the ion-exchange agents. It is one of the main features of the present invention to prepare the novel ion-exchange resins by activating a comparatively small molecule, carrying the desired chemical function, and to attach this to the polymer backbone of a predetermined polymeric carrier. The activation of the small molecule and its chemical bonding to the polymer substantially eliminates undesired side-reactions, and the product is obtained in a much improved form and has an enhanced degree of activity and specificity compared with similar agents prepared by the conventional sequence of reactions.

The products according to the present invention can be obtained in solid or in liquid form, as desired for certain specific purposes. There may be used a solid polymer backbone, or there may be used long-chain aliphatic compounds having a terminal functional group as carrier, and in the latter case liquid products are obtained.

The novel ion-exchange agents according to the present invention may be used for a wide variety of uses, depending on the functional moieties built into the molecule. They are effective agents for carrying out certain chemical reactions, such as acylations and the like; certain ion exchangers are effective agents for the selective removal of certain metal values from solutions of same; some may be used as ion exchange membranes, etc. Some of the products based on long-chain compounds can be used for liquid/liquid extractions, as their solubility in aqueous solutions is a very low one. Other and further features of the present invention will become apparent from the following description.

In our copending U.S. application Ser. No. 511,687, now U.S. Pat. No. 3,974,110, there is described and claimed a process for preparing certain reagents useful for effecting reactions of organic synthesis, of the general formula

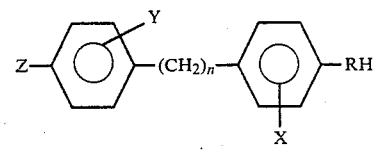

wherein
Z designates the

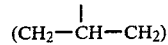

part of a polymeric backbone of a polymer like polystyrene, a copolymer comprising polystyrene and a comonomer like divinylbenzene, butadiene and other copolymers comprising styrene; or the aliphatic moiety of a long-chain aralkyl compound having a terminal phenyl or alkyl;

n is an integer of from 1 to 8, inclusive,

R designates oxygen or sulfur;

X designates nitro, carbonyl, carboxyl, cyano-carbalkoxy or a carboxamido group which may be substituted on the nitrogen atom, or a halogen atom, wherein Y is -H or a non-interfering substituent, and corresponding compounds with a naphthyl group instead of the

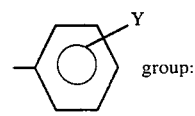 group:

The present invention relates to the preparation of further reagents of similar structure, but which are useful for certain uses not contemplated in our said first patent application.

The novel products of the present invention are prepared by chemically binding an activated chemical moiety to a polymer backbone, the term "polymer backbone" designating a solid polymer or a long-chain compound. The reaction can be schematically represented, by the reaction sequence

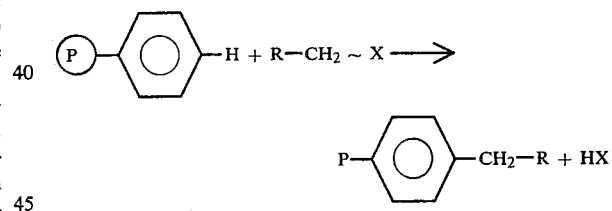

Wherein ⓟ designates the polymeric backbone as hereinbefore defined, which in the case of solids can be a polystyrene polymer of the type

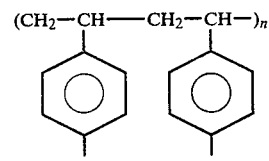

or a similar copolymer, such as for example with 2% D.V.B. or in the case of liquids it designates a long-chain compound, such as for example dodecyl benzene or the like, of the formula

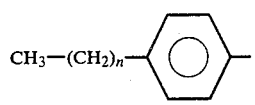

In the above X designates halogen such as —Cl —Br or —OH or —OR and R—CH$_2$— designates the desired functional moiety attached to the polymer backbone.

Weak acid and weak base ion exchange resins can be prepared by reacting a polymeric backbone, as defined above, with a chloromethylated chloro-nitro-benzene or with chloromethylated nitrobenzene, respectively, as shown schematically in the following reaction sequence:

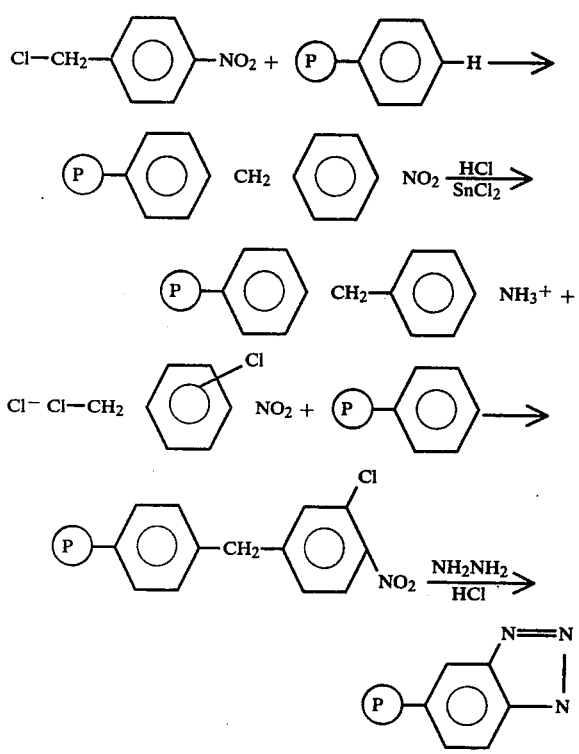

The above weakly acidic or weakly basic agents can be used as ion exchange resins.

Chelating Agents

Non-selective ion exchange agents according to the present invention can be converted into effective chelating agents by means of the Fries rearrangement:

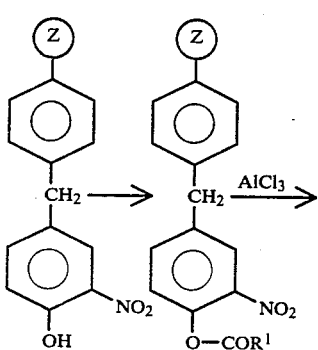

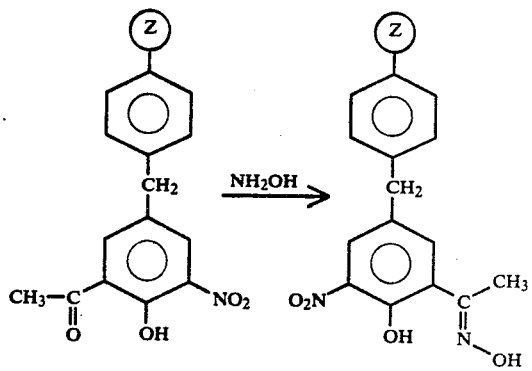

The 8-hydroxy-isoquinoline polymer can be esterified as above, and after the Fries rearrangement and conversion to the oxime there are obtained polymeric chelating agents useful in the removal of the recovery of metal values from solutions. The reaction sequence is schematically as follows:

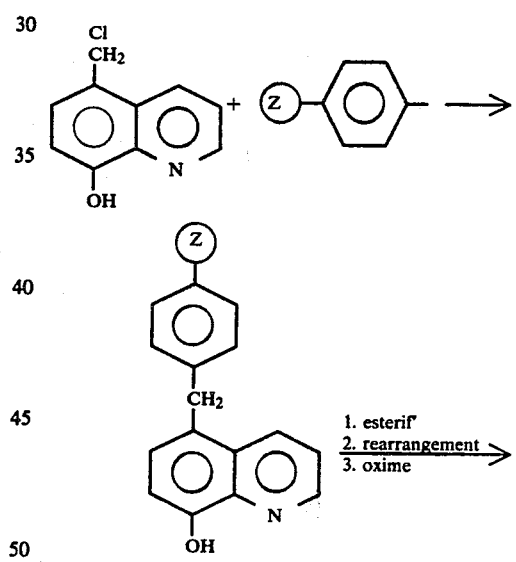

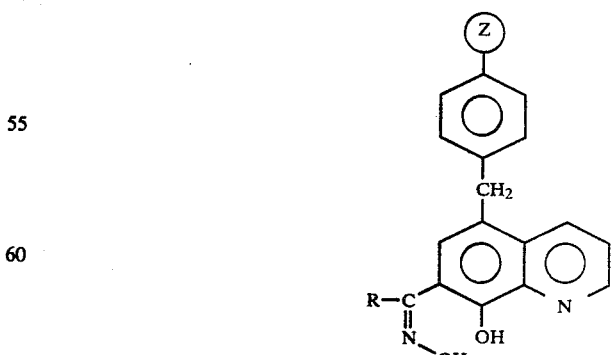

A further type of reagent was prepared by the reaction sequence set out in the following:

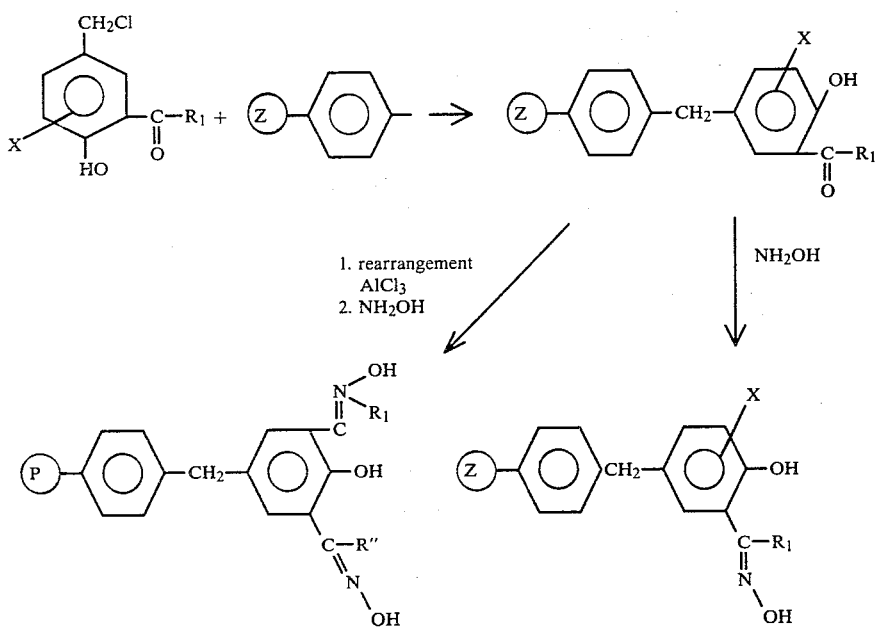

wherein

R₁ designates —H, alkyl or aryl;

X designates alkyl, aralalkyl, halogen, nitro, carboxyl, carboxaldehyde

R" designates —H, alkyl or aryl including substituted aryls.

Similar polymeric agents were prepared by conventional methods and it was found that the ones prepared by the reaction sequence according to the present invention had a higher degree of activity as evident from loading characteristics of the resin, (See U.S. Pat. No. 3,974,110) and that the physical shape and stability of the agents according to the present invention was much better. They were used for repeated sequences of metal removal and were found not to deteriorate.

EXAMPLE 1: 4-Nitrobenzylated Polystyrene

To a solution of 1.3 g aluminum chloride in 10 ml nitrobenzene there was added 1.7 g 4-nitrobenzyl chloride and 2 g of Xe-305 (polystyrene in bead dorm, Rohm & Haas, USA). The mixture was maintained at a temperature of 65° C. during 72 hours. At the end of this period of time the product was poured on 20 ml of a methanol/HCl mixture (1:1, Conc. HCl), washed with 20 ml of methanol and dried at 80° C. during 5 hours. A crop of the desired product of 3.0 g was obtained. It had a nitrogen content of 4.53% by weight.

EXAMPLE 2: 4-Aminobenzylated Polystyrene Hydrochloride

To a solution of 14 g stannous chloride hydrate in 20 ml ethanol and 20 ml concentrated aqueous hydrochloric acid there was added 3 g of the polymer obtained in Example 1. The mixture was maintained at a temperature of between 80°–90° C. during 20 hours, the resin was filtered off, washed with a warm mixture (1:1) of ethanol and conc. HCl, with 1 N HCl, with water and with acetone. The product was dried, and the nitrogen content was 4.59% and chlorine content was 6.35% by weight.

EXAMPLE 3: 4-Isocyanato-benzylated Polystyrene

The product of Example 2 was reacted in its hydrochloride form with phosgene at 60°–70° C. for 2 hours. The phosgene was driven off with a stream of nitrogen, the polymer was filtered off and washed with dry ether. A quantitative yield of the desired product was obtained.

The polyiscyanato substituted polymer reacts quickly with nucleophiles. Thus, for example, 2 g of the polymer eliminated quantitatively 1 mmole benzylglycine from a solution thereof in 10 ml chloroform.

The polyisocyanato polymer was reacted with hydrazine (2 g of the polymer with 2 g hydrazine in dioxan during 1 hour), yielding a quantitative yield of the corresponding semicarbazide. Analysis: nitrogen: 7.05%; chlorine: 0.51% (residual).

EXAMPLE 4: (3-Nitro-4-chloro) benzylated Polystyrene

To a solution of 10.4 g aluminum chloride in 120 ml nitrobenzene there was added 19.1 g 3-nitro-4-chloro benzylchloride followed by 16 g of Xe-305 resin, and the mixture was maintained at 90° C. during 3 days. The resin was poured on a methanol/hydrochloric acid (1:1, conc. Hcl) mixture, washed with methanol, with dimethyl-formamide, methanol, and with water. A crop of 20.7 g of dry product was obtained having a nitrogen content of 1.82% by weight.

EXAMPLE 5: (3-Nitro, 4-hydroxy; 5acetyl)benzylated Polystyrene 5 g (3-nitro, 4-hydroxy) benzylated polystyrene cross-linked with 2% divinylbenzene of mesh size 200–300 was converted into the acetate by leaving in a solution of excess acetic anhydride and pyridine in 50 ml methylene chloride until the resin lost its yellow color. It was filtered off, washed with methylene chloride and desiccated overnight over phosphorus pentoxide under a high vacuum. The thus obtained (3-nitro, 4-acetoxy) benzylated polystyrene was left in a solution of 1.3 g aluminum chloride in 25 ml nitrobenzene at 65°

C. for 24 hours. The product was poured on a methanol/hydrochloric acid mixture (1:1, conc. Hcl), filtered off, washed with methanol, with water, with methanol and dried. The yellow product shows a carbonyl at 1695 cm$^{-1}$.

By the same procedure a similar resin was prepared, starting with macroporous Xe-305. It had a nitrogen content of 2.55% by weight.

EXAMPLE 6: (8-Hydroxy-quinoline)-5-benzylated Polystyrene (not part of the invention)

2 g of dry chloromethylated polystyrene (Xe-305) were reacted with 1.2 g of 8-hydroxyquinoline and 1.35 g aluminum chloride in 20 ml nitrobenzene at 70° C. for 20 hours, during which time the hydroxyquinoline dissolved. The resin as filtered off, washed with methanol: with hydrochloric acid (1 N), with sodium hydroxide (0.5 N), with water, with acetone and dried. There was obtained a crop of 2.0 g of the desired product which had a nitrogen content of 2.4% by weight.

EXAMPLE 7: (8-Hydroxy-quinoline)-5-benzylated Polystyrene

According to a preferred embodiment, there are reacted 2.5 g aluminum chloride. 2.4 g 5-chloromethyl-8 hydroxyquinoline and 2.0 g of Xe-305 polystyrene resin in 10 ml of nitrobenzene. The reaction was carried out at 60° C. and during 20 hours. The resulting resin was filtered off, washed with HCl/methanol (1:1, conc. Hcl), with methanol, water, methanol and ether. The dry product had a nitrogen content of 1.79%. A crop of 3.0 g was obtained.

The resulting 8-hydroxyquinoline resins can be loaded with amino acids and this can be used for the synthesis of peptides. 1.1 g of the polymer obtained in the present example in its hydrochloride form was reacted with 10 ml of a solution of 5%, triethylamine in chloroform until it lost its yellow color, filtered off, washed three times with chloroform and introduced into a solution of 0.8 g BOC-alanine in 25 ml dimtehylformamide. The reaction mixture was cooled to 0° C., 0.8 g dicyclohexylcarbodiimide (DCC) was added and left to stand overnight. The resin was filtered off, washed and dried. The loading, as determined by the benzylamine method, was 0.7 mmole/g.

A comparison of the resins obtained according to Examples 6 and 7 shows that the resin obtained according to Example 7 is mechanically stable and colorless after neutralization while that of Example 6 is colored and decomposes upon prolonged storage.

EXAMPLE 8: (4-hydroxy, 3-acetyl) benzylated Polystyrene

To a solution of 1.8 g aluminum chloride in 100 ml nitrobenzene there was added 2 g of Xe-305 polystyrene polymer; the reaction mixture was brought to 60° C. and during 48 hours there was added dropwise a quantity of 1.8 g 2-acetyl-4-chloromethyl phenol in 100 ml nitrobenzene. After stirring for additional 20 hours the polymer was poured into HCl (2 M), filtered off, washed with methanol, with water, with methanol and dried. A crop of 2.4 g of the desired product was obtained, having a content of 1 mmole -OH groups/g polymer; IR absorption at 1640 cm$^{-1}$, (KBr).

EXAMPLE 9: (2,6-Dichloro-3-acetyl-4-hydroxy) and (2,4-dichloro-5-hydroxy-6-acetyl) benzylated Polystyrene To a solution of 1.7 g aluminum chloride in 10 ml nitrobenzene there was added 2.3 g of chloromethyl-2,4-dichloro-6-acetyl phenol (isomeric mixture) and 2.0 g Xe-305 resin. The mixture was kept at 70° C. for 48 hours, poured on hydrochloric acid (2 M) and the resin was filtered off, washed with methanol, with water, with methanol and dried. A quantity of 2.35 g of the desired product was obtained.

EXAMPLE 10: 3-Nitro-4-hydroxy-benzylated toluene.

1 Millimole of 3-nitro-4hydroxy-benzyl chloride was reacted with excess of toluene in 1.8 M aluminum chloride in 20 ml of nitrobenzene at 65° C. for 20 hours. The product was diluted with toluene and washed with hydrochloric acid (1 N), water, and the nitrobenzene was removed by steam distillation leaving an oily substance which crystallized upon standing. IR: 1690 cm$^{-1}$;

NMR: 2.3 ppm (3H) absorption of methyl; 4.2 ppm (2H) absorption of methylene.

EXAMPLE 11: 3-Nitro, 4-hydroxy-benzylated Dodecylbenzene, 6.2 g (25 mmoles) dodecylbenzene and 5.7 g of 3-nitro-4-hydroxy benzylchloride were reacted with 3.6 mmoles aluminum chloride in 20 ml nitrobenzene as set out in Example 10. There was obtained a yield of 8.9 g of an oily substance. The IR and NMR spectra were in accordance with the expected formula.

Example 12: (8-Hydroxyquinoline)-5-benzylated cyclododecylbenzene.

1 g 5-Chloromethyl-8-hydroxyquinoline and 1 g cyclododecylbenzene were reacted with 1 g aluminum chloride in 10 ml nitrobenzene at 60° C. during 3 hours. After dilution with 40 ml of chloroform the product was washed with water, the chloroform was removed and the product crystallized from nitrobenzene. There was obtained 1.2 g of yellow crystals. The NMR and IR spectra confirm the expected formula.

EXAMPLE 13: Preparation of Benzhydroxytriazole Polymer

Stage A 10 g of Xe 305 polystyrene were added to 13 g 3-nitro-4-chlorobenzyl alcohol and 10 g aluminum chloride in 50 ml benzene. The reaction mixture was left at 70° C. for 3 days, poured on ice-water washed with methanol, hydrochloric acid (1 N), methanol, and dioxan and the product was dried. There was obtained 14.3 g of a colorless polymer containing 7.0% chlorine.

Stage B 10 g of the product of Stage A were refluxed in 40 ml hydrazine hydrate (98%) and 60 ml 2-ethoxyethanol. The reflux was effected during 1 hour and after this period the polymer was filtered off, washed with water, with dioxan, methanol, ether and dried. The product contains 0.4% Cl, and 5.4% nitrogen.

Stage C

The product of Stage B was mixed with 50 ml concentrated hydrochloric acid and 50 ml dioxane and stirred at room temperature for 20 hours. The polymer was filtered off, washed with water, dioxan, methanol, ether and dried. The desired benzhydroxytriazole polymer (BHT) was obtained in quantitative yield. Nitrogen content: 5.2%

Example 13: A. Triphenylmethyl Polymer

A quantity of 5 g polystyrene (Xe 305 Rohm & Haas) was reacted with 10 g benzhydrol in a 1.8 M solution of aluminum chloride in nitrobenzene (20 ml). The reaction was carried out at 75° C. during 20 hours. The reaction mixture was worked up as in Example 1 and there was obtained 0.9 g of the desired product, 2 mmole/g of the polymer.

B. 4-Chlorobenzylated Polystyrene

In a similiar manner, 5 g of polymer were reacted with 5 g of chlorobenzyl chloride to give 6.6 g of 4-chlorobenzylated polystyrene containing about 2 mmole chlorine per gram of polymer.

C. Polypyridine Polymer

A quantity of 1.2 g of 3-pyridyl carbinol in 15 ml of 1.8 M aluminum chloride in nitrobenzene was reacted with 2 g Xe-305 during 3 days at 80° C. The polymer was poured on methanol, filtered off and washed with HCl methanol, aqueous methanol, methanol and ether. A crop of 2.6 g of the desired product was obtained which contained 3.6% nitrogen.

D. 3-Pyridyl Tolylmethane

A quantity of 1.2 g 3-pyridyl carbinol in 15 ml 1.8 M aluminum chloride in nitrobenzene was reacted with 10 ml of toluene during 3 days at 80° C. The reaction mixture was poured on HCl/ice and extracted with toluene. The organic phase was washed with water, dried and the solvent was evaporated. The desired product was obtained as viscous oil, containg 8.5% nitrogen.

E. 4-Hydroxy-3-formyl Benzylated Polystyrene

The preparation was carried out as in Example 8, but with 2-formyl-4-chloromethyl phenol.

F. 4-Hydroxy-3-formyl benzylated Toluene.

The preparation was according to Example 8 and a similar yield of the desired product was obtained.

EXAMPLE 14: Fries Rearrangement of Phenol Esters.

The acetoxy derivatives of the phenols were prepared by leaving them in a methylene chloride solution of acetic anhydride (from 1:1 to 1:2), and pyridine (1 to 10%), until decolorization has taken place. The resins were filtered off, and washed with methylene chloride. The liquids were washed with water, concentrated hydrochloric acid, water, and the solvent was evaporated. The samples were left in a dessicator under vacuum, over phosphorus pentoxide, for a period of 20 hours. Other esters were prepared in a similar manner.

The rearrangement was effected at a temperature in the range of between 45°-100° C., preferably at about 65° C., by leaving the esters in a nitrobenzene solution of aluminum chloride. Good results were obtained with a 1.8 M aluminum chloride solution by leaving for about 20 hours. The resulting polymers were filtered off, washed with methanol, concentrated hydrochloric acid, methanol and ether.

The liquids were diluted with ether (about 5 ml per 1 ml of liquid), washed with concentrated hydrochloric acid, water and the solvent was evaporated. All the liquid products could be identified by the presence of acetylic hydrogens in the NMR spectra. The acetylic hydrogens were in the region of 2.0-25 ppm and there exists the typical shift of the 1750 cm$^{-1}$ acetoxy absorption to the 1690-1700 cm$^{-1}$ aromatic ketone absorption. In addition the corresponding oximes and dinitrophenol derivatives were prepared. The following acylated derivatives were prepared:

(3-Nitro-4-hydroxy-5-acetyl) benzylated polystyrene of both the 2% D.V.B.-polystyrene type, and Xe-305. Oxime: % N 2.7; DNP: % N 5.4

(3-Nitro-4-hydroxy-5-acetyl) benzylated toluene (3-Nitro-4-hydroxy-5-acetyl) benzylated dodecylbenzene 5-(7-Acetyl-8-hydroxyquinoline) benzylated polystyrene 5-(7-Acetyl-8-hydroxyquinoline)-benzylated cyclododecylbenzene (3-Nitro-4-hydroxy-5-benzoyl) benzylated polystyrene (3-Nitro-4-hydroxy-5-p-nitrobenzoyl) benzylated polystyrene

EXAMPLE 15: Preparation of Oximes

The oximes were prepared starting with the acylated polymers (containing about 4 mmole acyl groups per 2 g of polymer). These were refluxed with hydroxylamine hydrochloride. Good results were obtained by using 10 ml of an ethanolic solution containing 1.4 ml (10 mmole) triethylamine and 0.7 g (10 mmole) hydroxylamine hydrochloride and the reflux was effected during 20 hours. The polymer was filtered off, washed with warm ethanol, with dilute acid and with water.

Liquid oximes were prepared by the same procedure; the product was taken up in benzene, washed with dilute acid and with water. Upon evaporation of the solvent, the desired products were obtained as oily substance.

The products showed the typical IR-absorption in the region of 1660-1640 cm$^{-1}$ with the disappearance of the carbonylic band at 1690 cm$^{-1}$.

In this manner the following oximes were prepared:

A. Oxime of (3-Nitro-4-hydroxy-5-acetyl) benzylated polystyrene (Xe-305 polymer: analyses 4.28% N).

B. Oxime of (3-Nitro-4-hydroxy-5-acetyl) benzylated dodecylbenzene (1.8% N).

C. Oxime of (7-Acetyl-8-hydroxy-quinoline)-5-benzylated polystyrene) (analysed 2.74% N).

D. Oxime of (4-Hydroxy-3-acetyl) benzylated polystyrene (analyses 1.61% N).

E. Oxime of (2,6-dichloro-3-acetyl-4-hydroxy and (2.4-dichloro-5-hydroxy-6-acetyl) benzylated polystyrene (analyses 1.28% N).

F. Oxime of (7-Acetyl-8-hydroxyquinoline) benzylated cyclododecylbenzene.

G. Oxime of (4-hydroxy-3-acetyl) benzylated dodecylbenzene.

H. Oxime of (4-hydroxy-3-Formyl) benzylated dodecylbenzene.

I. Oxime of (4-hydroxy-3-formyl) benzylated polystyrene.

EXAMPLE 16: Extraction of Metals.

The following aqueous solutions were tested:

a. 2.1 g/l Cu as copper sulphate, 0.5 M $Na_2SO_4$, pH 1.3
b. 2.1 g/l Cu as copper sulphate, 0.5 M $Na_2SO_4$, pH 2.12
c. 2.1 g/l Cu as copper sulphate, 0.5 M $Na_2SO_4$, pH 2.72
d. 1.525 g/l $CuSO_4$; pH 2.42

0.22 g/l Cu(NH$_3$)$_4$SO$_4$, PH 9.5
f. 2.1 g/l FeCl$_3$, pH 2.8
g. 1.45 g/l FeCl$_3$ in conc. phosphoric acid The extraction was effected by shaking the solutions for 2 minutes in a separatory funnel with solutions of the reagents in chloroform at 1:1 ratio. The phases were separated and the organic phase was washed with 0.01 N sulfuric acid. After this the stripping was effected by means of 2 M H$_2$SO$_4$ at a 1:1 ratio (by volume). The results are given in Table No. 1. The analysis was by means of atomic absorption spectrometry.

Solutions (d) and (e) were used for copper, (f) and (g) for iron. The tests were conducted as follows: a resin bed was prepared by inserting about 2 g of dry resin into a column of 10 mm diameter. The solutions were passed at a rate of 1 ml/minute, the resin was washed with 0.01 N H$_2$SO$_4$ and then stripped by means of 2 M H$_2$SO$_4$. The results are given in Table No. 2.

| Reagent Ex. No. | % of reagent | No. of solution | A:O | pH | % Extraction |
|---|---|---|---|---|---|
| 15/F | 5 | a | 1:1 | 1.3 | 76 |
| 15/F | 5 | b | 1:1 | 2.12 | 81 |
| 15/B | 5 | a | 1:1 | 1.3 | 90 |
| 15/B | 5 | b | 1:1 | 2.12 | 100 |
| 15/B | 5 | e | 1:1 | 9.5 | 99 |
| 15/G | 8 | d | 1:2 | 2.42 | 30 |
| 15/G | 8 | e | 1:1 | 9.5 | 100 |
| 15/G | 8 | f | 1:1 | 2.8 | 0 |
| 15/H | 6 | d | 1:2 | 2.4 | 12 |
| 15/H | 6 | e | 4:1 | 9.5 | 57 |
| 15/H | 6 | f | 1:1 | 2.8 | 0 |
| 21/d | 5 | a | 1:1 | 2.4 | 88 |
| 21/d | 5 | a | 5:1 | 2.4 | 88 |
| 21/d | 5 | e | 5:1 | 9.5 | 10 |

TABLE 2:
Absorption of Copper and Iron by Chelating Resins

| Resin acc. to Example No. | Metal | Solution | pH | Loaded mg/g resin |
|---|---|---|---|---|
| 7 | Cu | d | 2.42 | 12 |
| 7 | Fe | f | 2.8 | 3 |
| 7 | Fe | g | | 0.6 |
| 15/C | Cu | d | 2.42 | 6.3 |
| 15/C | Cu | e | 9.5 | 9.7 |
| 15/C | Fe | f | 2.8 | 1.1 |
| 15/A | Cu | d | 2.42 | 0.2 |
| 15/A | Cu | e | 9.5 | 5.3 |
| 15/A | Fe | f | 2.8 | 0.9 |
| 15/i | CU | d | 2.42 | 0.7 |
| 15/i | Cu | e | 9.5 | 11 |
| 15/i | Fe | f | 2.8 | 1.2 |
| 15/D | Fe | g | — | — |
| 15/D | Cu | d | 2.42 | 0 |
| 15/D | Cu | e | 9.5 | 5 |

EXAMPLE 17: Kinetics of Resin Loading and Elution

The resin used was that prepared according to Example No. 7 A quantity of 1 g of the resin was stirred in 10 ml of Solution (d) of Example 16, at a pH of 2.42. Aliquots were removed and tested. The resin was then separated and stripped by means of 10 ml 2 M sulfuric acid.

TABLE 3:
Rate of Absorption and Elution

| Time (min) | Loading Conc. of Solution | Stripping (ppm) |
|---|---|---|
| 1 | 830 | — |
| 5 | 570 | 900 |
| 10 | — | 910 |
| 15 | 450 | 960 |
| 25 | — | 1120 |

Loaded: 9 mg total stripped 11.2
Resin: Ex. No. 7

A quantity of 2 g resin prepared according to example 7 was stirred in 100 ml of Solution (e) of Example 16 of pH 9.5. The stirring was carried out as indicated and after this period of time the resin was washed and stripped with 10 ml of 2 M sulfuric acid. The results are given in Table 3:

TABLE 3:

| Time (min) | conc. (ppm) in solution Loading | Stripping |
|---|---|---|
| 0 | 220 | — |
| 13 | — | 970 |
| 5 | — | 1050 |
| 6 | 190 | — |
| 10 | — | 1200 |
| 15 | 150 | — |
| 50 | 110 | — |

EXAMPLE 18: (8-Hydroxyquinoline)-5-Benzylated Toluene

The preparation was effected as in Example 7, but starting with 20 ml toluene instead of 2.0 g of Xe-305.

The work-up was as follows: Water was added, the organic phase was washed with water, dried and after this excess of solvent was removed under reduced pressure.

EXAMPLE 19: (4-Hydroxy-3-acetyl) Benzylated Toluene

The preparation was as in Example 8, but starting with 20 ml of toluene. The reaction mixture was worked up as in the preceding example.

EXAMPLE 20: Extraction of Uranylsulfate with 3-pyridyl-tolylmethane

A solution was prepared, containing 5 g of the above reagent per 100 ml toluene. The thus obtained solution was used at a volume ratio of 1:1 to extract U$_3$O$_8$ from an aqueous solution of same containing 1 g/l uranyl sulfate. The extraction was at a pH of 2.0 and 80% of the uranyl ions were extracted.

Example 21

In a manner similar to that of Example 15, the oximes of the compounds
a. (4-hydroxy-3-formyl) benzylated polystyrene;
b. (4-hydroxy-3-formyl) benzylated toluene;
c. (8-hydroxyquinoline) 5-benzylated toluene and of
d. (4-hydroxy-3-acetyl) benzylated toluene
were prepared.

Solutions of the compound of Example 21(d) were used for extracting metals according to Example 16. A 5% solution of the reagent was used.

With Solution a, at a A:O ratio (defined in Example 16) of 1:1 at pH 2.4 an extraction of 88% was obtained.

The same system, but at A:O of 5:1 gave the same extraction.

Solution No. 5 at an A:O ratio of 5:1 at pH 9.5 gave an extraction of 100%.

We claim:

1. A chelating agent of the formula

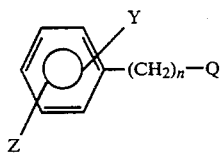

wherein Z is alkyl or aralkyl, the aliphatic portion of which being long-chain alkyl and the aryl portion of which being terminal phenyl; Q is

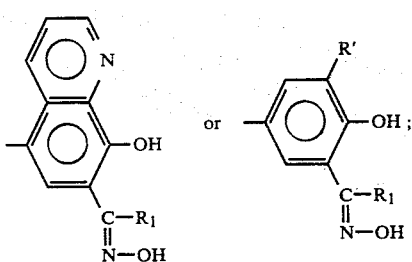

$R_1$ is H, alkyl or aryl; R' is H, alkyl, aralkyl, hydrogen, nitro, carbonyl or carboxaldehyde; n is an integer of from 1–15; and Y is H.

2. A chelating agent in accordance with claim 1 wherein Z is $CH_3$, dodecyl, or cyclododecyl, Y is hydrogen, $R_1$ is hydrogen or methyl, and R' is hydrogen or nitro.

3. A chelating agent in accordance with claim 1 of the formula

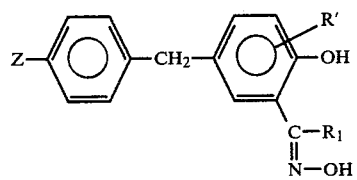

4. A composition of matter of the formula wherein Z is alkyl or aralkyl, the aliphatic portion of which being long-chain alkyl and the aryl portion of which being a terminal phenyl; $R_1$ is H, alkyl or aryl; and R" is H, alkyl or aryl.

* * * * *

UNITED STATES PATENT AND TRADEMARK OFFICE
CERTIFICATE OF CORRECTION

PATENT NO. : 4,215,219  Page 1 of 5
DATED : July 29, 1980
INVENTOR(S) : Patchornik et al.

It is certified that error appears in the above-identified patent and that said Letters Patent are hereby corrected as shown below:

In the Abstract, left column, the formula of lines 5-6 should
read -- (CH$_2$-CH-CH$_2$) --

In the Abstract, right column, the first structural formula
should read:

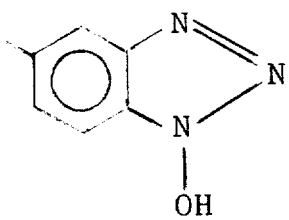

In the Abstract, right column, the fourth structural formula
should read:

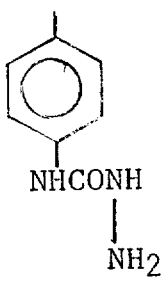

In the abstract, right column, the seventh structural formula
should read:

UNITED STATES PATENT AND TRADEMARK OFFICE
CERTIFICATE OF CORRECTION

PATENT NO. : 4,215,219
DATED : July 29, 1980
INVENTOR(S) : Patchornik et al.

It is certified that error appears in the above-identified patent and that said Letters Patent are hereby corrected as shown below:

In the Abstract, second page, left column, the structural formul should read:

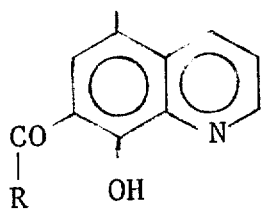

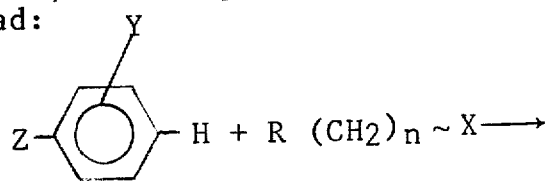

In the Specification, column 2, the third structural formula should read:

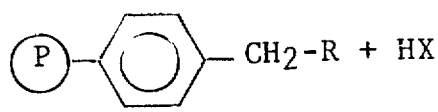

In the specification, column 2, the fourth structural formula should read:

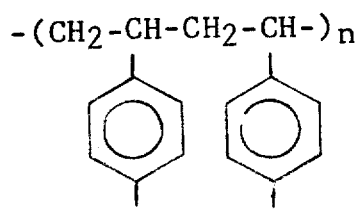

UNITED STATES PATENT AND TRADEMARK OFFICE
CERTIFICATE OF CORRECTION

PATENT NO. : 4,215,219
DATED : July 29, 1980
INVENTOR(S) : Patchornik et al.

It is certified that error appears in the above-identified patent and that said Letters Patent are hereby corrected as shown below:

Column 3, the second structural formula should read:

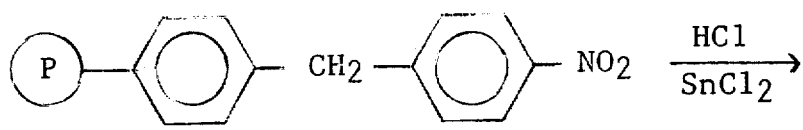

Column 3, the third structural formula should read:

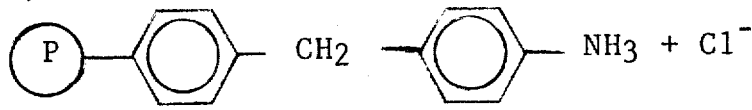

Column 3, the fourth structural formula should read:

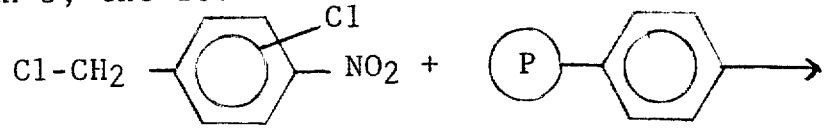

Column 3, the sixth structural formula should read:

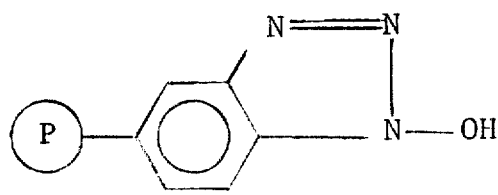

Column 5, left column, that part of the structural formula reading (P)— should read (Z)— same formula, that part of the formula reading

UNITED STATES PATENT AND TRADEMARK OFFICE
CERTIFICATE OF CORRECTION

PATENT NO. : 4,215,219
DATED : July 29, 1980
INVENTOR(S) : Patchornik et al

It is certified that error appears in the above-identified patent and that said Letters Patent are hereby corrected as shown below:

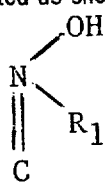 should read 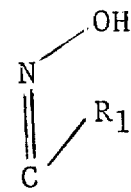

Claim 1, first structural formula, that part of structural formula 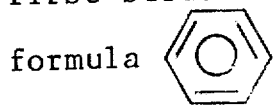 should be 

Claim 1, second structural formula, that part of the formula 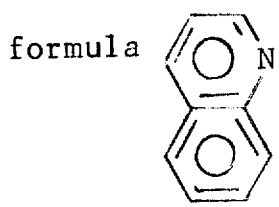 should read 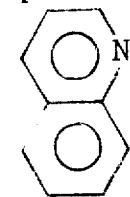

Claim 1, third structural formula, that part of the formula 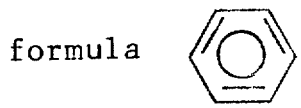 should read 

Claim 3, that part of the structural formula reading

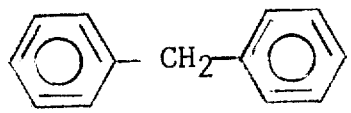

UNITED STATES PATENT AND TRADEMARK OFFICE
CERTIFICATE OF CORRECTION

PATENT NO. : 4,215,219
DATED : July 29, 1980
INVENTOR(S) : Patchornik et al

It is certified that error appears in the above-identified patent and that said Letters Patent are hereby corrected as shown below:

should read:

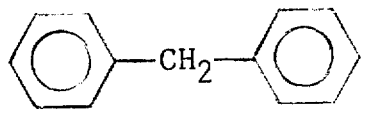

Signed and Sealed this

Seventeenth Day of March 1981

[SEAL]

Attest:

RENE D. TEGTMEYER

Attesting Officer — Acting Commissioner of Patents and Trademarks